United States Patent [19]

Strom

[11] Patent Number: 4,649,741
[45] Date of Patent: Mar. 17, 1987

[54] INSITU SOIL SHEAR MEASUREMENT APPARATUS

[75] Inventor: James A. Strom, Whittier, Calif.
[73] Assignee: Geomatic, Whittier, Calif.
[21] Appl. No.: 768,452
[22] Filed: Aug. 22, 1985
[51] Int. Cl.[4] ............................................. G01N 3/00
[52] U.S. Cl. ............................................. 73/84; 73/784
[58] Field of Search ................ 73/784, 843, 767, 847, 73/84, 862.32, 862.33, 862.35; 175/40

[56] References Cited

U.S. PATENT DOCUMENTS

| | | | |
|---|---|---|---|
| 2,907,204 | 10/1959 | Gibbs | 73/101 |
| 3,364,734 | 1/1968 | Wilson | 73/101 |
| 3,465,576 | 9/1969 | Spanski | 73/84 |
| 3,561,259 | 2/1971 | Barendse | 73/784 |
| 3,691,825 | 9/1972 | Dyer | 73/862.35 |
| 3,709,031 | 1/1973 | Wilson et al. | 73/843 |
| 3,717,029 | 2/1973 | Tveter | 73/862.35 |
| 3,855,853 | 12/1974 | Claycomb | 175/40 |
| 4,398,414 | 8/1983 | MacGregor | 73/84 |
| 4,411,160 | 10/1983 | Lutenegger | 73/843 |

OTHER PUBLICATIONS

Oberg, "The Determination of Stresses in Oil Well Casing in Place", Jan. 1950, API Paper.

Primary Examiner—Stewart J. Levy
Assistant Examiner—Robert R. Raevis
Attorney, Agent, or Firm—Pretty, Schroeder, Brueggemann & Clark

[57] ABSTRACT

A testing apparatus for measuring soil shear strength which includes a torque motor connected to a torque shaft, torque cell and vane which extend beneath the soil surface. The torque cell is located between the shaft and the vane; and measures soil shear strength. It includes a torque transmission member on which an electrical transducer is mounted; and a housing which surrounds the transmission member and defines an annular cavity which protectively surrounds the transducer.

1 Claim, 2 Drawing Figures

INSITU SOIL SHEAR MEASUREMENT APPARATUS

FIELD OF THE INVENTION

This invention relates generally to devices for measuring the physical characteristics of soil and, more particularly, to devices for measuring insitu the shear strength of soil.

BACKGROUND OF THE INVENTION

A determination of soil shear strength is important in a number of scientific and engineering applications. It is often sought of necessity in the areas of structural and geological engineering. Soil shear strength data, for example, may dictate whether a particular structure can be securely built at a chosen location. Or, it may influence the design parameters of a building foundation or a toxic substance landfill. It is also rather commonly used in dam construction and dredging operations. Finally, soil shear strength data is a significant consideration in earthquake prediction and analysis.

Early devices for determining soil shear strength were suitable for laboratory, rather than insitu, testing of a soil sample. It was recognized, however, that significant margins of error were sometimes introduced by the removal of the soil sample from its environment. This was particularly so in the case of dredging operations and dam construction. Consequently, it was highly desirable to have a device capable of measuring insitu the shear strength of soil.

In this context, a number of techniques have been developed. One such technique, described in U.S. Pat. No. 4,411,160 involves an apparatus having measurement devices located on the blades of a vane inserted in the soil. Here, the apparatus includes an above-surface torque motor which is connected to the vane by one or more sub-surface shafts. The vane blades have cavities in which strain gages are disposed. When the torque motor applies torque to the shafts and the vane, each gage measures the stresses acting on a portion of the corresponding blade. Afterwards, a mathematical calculation based on the respective stress measurements for each gage results in an approximation of soil shear strength.

This technique, however, has significant drawbacks. In particular, the location of the strain gages on the blades of the vane makes it relatively complex and difficult to change or replace the vane. Moreover, each strain gage simply measures the stresses acting on a portion of the corresponding blade, rather than on the vane as a whole.

Another technique, described in U.S. Pat. No. 2,907,204, involves the mounting of a strain gage to a component of the torque motor at the top of the shaft. The soil shear strength measurement is thus made at the surface. While this procedure has certain advantages compared to placing strain gages on the blades of the vane, it too has drawbacks.

In particular, it is necessary to compensate for frictional forces stemming from, among other things, the shaft support bearings and the rubbing of the soil against the rotating shaft. These forces increase as the length of the shaft increases. For best results, it is thus necessary to take frictional measurements at varying depths along the shaft to compute frictional effects.

Accordingly, there is a need for a device capable of more accurately measuring insitu the shear strength of soil, and doing so simply, economically and accurately.

SUMMARY OF THE INVENTION

The present invention, which fulfills the above need, includes a torque motor located at the soil surface, a torque shaft, a vane and a torque cell attached to the vane beneath the soil surface. The motor causes the vane to apply torque to the surrounding soil, the shear strength of which is to be determined. The torque cell, located between the shaft and the vane, determines soil shear strength by a measurement of the torque transmited.

The measurements made at the torque cell are substantially unaffected by the friction that is unavoidable in the torque shaft support bearings and in the soil rubbing against the torque shaft as it rotates. As such, the measurements taken need not be modified through the application of either corrective frictional equations or extrapolation techniques to compensate for the effects of friction. Moreover, there is no need to manipulate and analyze numerous measurements from various sources to assess soil shear strength.

The torque cell includes an electrical transducer which measures and electronically transmits the torque applied to the cell. The transducer may be a strain gage and may include at least one piezoelectric element.

The torque cell further comprises a torque transmission member on which the transducer is mounted. Preferably, a housing surrounds the transmission member and defines an annular cavity surrounding the transducer. The housing may be generally cylindrical and is rotatable at one end through a small angle relative to the transmission member, but produces negligible frictional inaccuracy. The annular cavity protects the transducer against moisture, abrasion and undesirable thermal gradients in the surrounding soil, all of which might otherwise impair the accuracy of a torque measurement.

The torque cell may advantageously have a large diameter portion nearer to the torque shaft and a small diameter portion nearer to the vane. The large diameter portion receives a fitting which secures the shaft to the transmission member. The small diameter portion is where maximum angular deflection occurs. A measurement of the torque acting on this portion best indicates the soil shear strength in the vicinity of the vane.

The torque cell further includes a lower seal located between the housing and the small diameter portion and an upper seal located between the housing and the large diameter portion. The seals facilitate the quick removal of the housing when the transducer must be replaced.

The transmission member can define a generally cylindrical chamber which receives the fitting and a cable. The cable extends from the soil surface and passes through a central cavity in the fitting before being received by the chamber.

Within the chamber there is a conductive tube. One end of the tube is connected to a wire leading from the transducer and the other end to another wire which passes through the cable and is connected with the cable to an output device on the surface. The chamber is further filled with an encapsulation material which shields the wires from moisture and keeps them attached to the tube. The wire leading from the transducer may also pass through a tubular passageway defined by the large diameter portion of the transmission member before being connected to the tube.

Other features and advantages of the present invention will become apparent from the following description of the preferred embodiments, taken in conjunction with the accompanying drawings, which illustrate, by way of example, the principles of the invention.

BRIEF DESCRIPTION OF THE DRAWINGS

The accompanying drawings illustrate the invention. In such drawings.

DESCRIPTION OF THE PREFERRED EMBODIMENT

Figure 1:
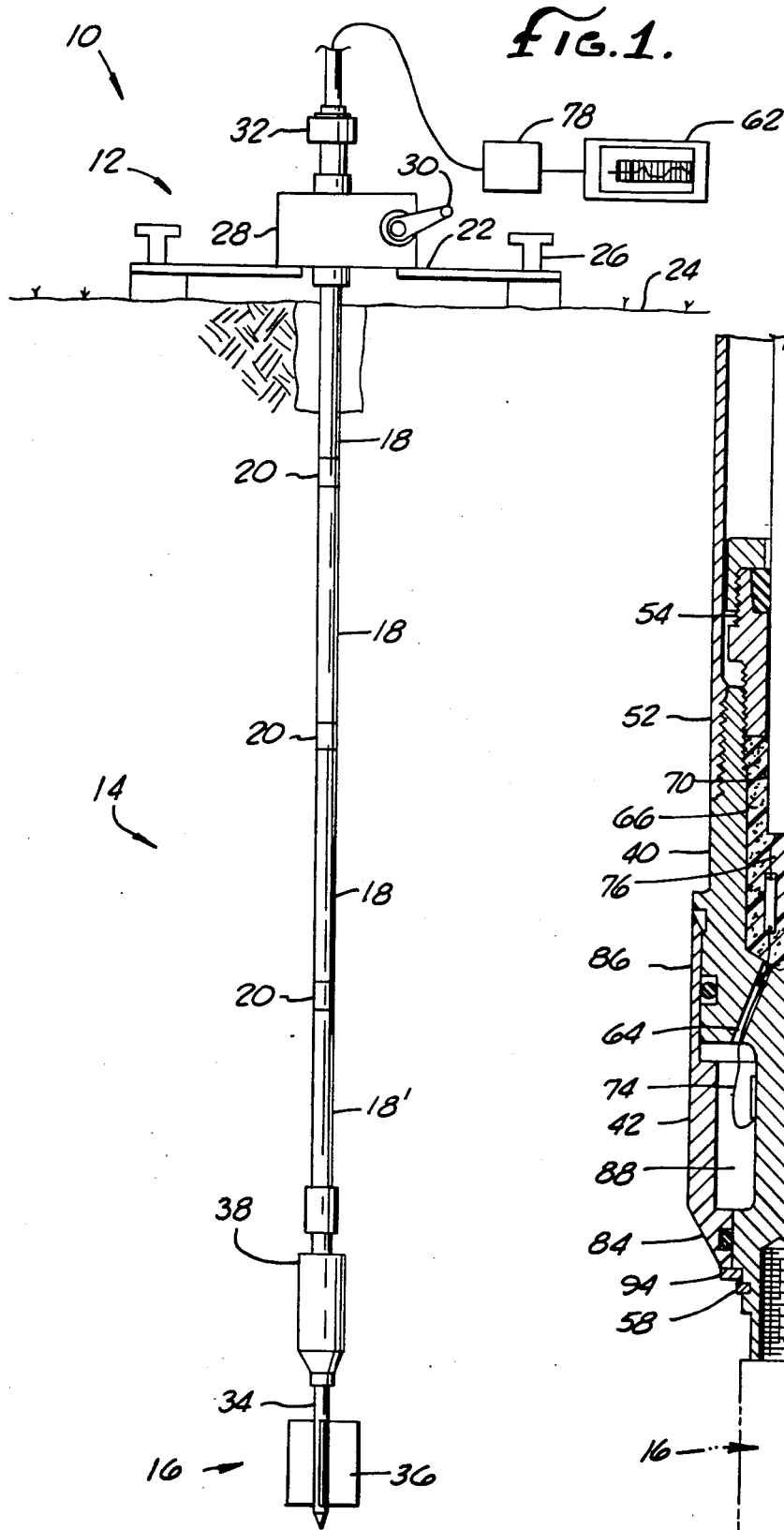
FIG. 1 is a partially schematic side elevation of a soil shear strength testing apparatus for measuring insitu the shear strength of soil and embodying a torque cell according to the present invention.

A testing apparatus 10 for measuring insitu the shear strength of soil, according to the present invention, includes a torque motor 12 postioned on a soil surface 24. The motor 12 has a central vertical torque shaft 14, as shown in FIG. 1, and causes a vane 16 to apply torque to the surrounding soil. The torque shaft may have a string of rods 18 secured end to end by couplings 20. The motor 12 rests on a supporting base 22 which is secured to the soil surface 24 by an array of anchors 26 (only two of which are shown). The supporting base 22 and the anchors 26 stabilize the entire apparatus 10.

The torque shaft 14 is often positioned through insertion in a pre-drilled bore. However, where the soil is soft, such as in dredging operations, it can usually be pushed beneath the surface 24 to a desired depth without pre-drilling. In that event, a shallow hole may be dug to facilitate entry of the vane 16 into the soil.

It will be appreciated that the apparatus 10 shown in FIG. 1 may include various known types of torque motors and vanes depending on the soil conditions and tests to be made. By way of example, the torque motor 12 of FIG. 1 includes a worm gear reducer 28 which is manually operated by a crank 30. The torque shaft 14 is also preferably gripped by an adjustable and slidable collet 32. The collet 32 locks the torque shaft 14 during operation and permits it to slide vertically during positioning to accommodate different measurement depths.

The type of vane 16 selected will often depend on the physical characteristics of the soil when shear strength is to be measured and the soil depth at which shear strength measurements are to be taken. By way of example, the vane 16 of FIG. 1 includes a vane shaft 34 having four radially extending blades 36, two of which are shown in the drawings. The blades 36 may have any varying dimensions, depending on the testing conditions.

When the testing apparatus 10 has been completely set up, the operation commences with the turning of the crank 30 by the motor 12. The reducer 28 then rotates the torque shaft 14 which transmits torque to the vane 16. The vane 16 then applies torque to the surrounding soil in which it is embedded.

In accordance with the present invention, a means for measuring this torque applied by the vane 16, and the corresponding soil shear strength, is embodied in a torque cell 38 shown in FIG. 1. The torque cell 38 is positioned immediately above the vane 16, connected at one end to the torque shaft 14 and at the opposite end to the vane shaft 34.

The torque cell 38 of this exemplary embodiment will now be more particularly described with reference to FIG. 2. It includes an elongated torque transmission member 40 partially surrounded by a housing 42. The torque transmission member 40 transmits torque from the torque motor 12 to the vane 16. It includes a large diameter portion 44 nearer to the torque shaft 14 and an axially aligned small diameter, or necked down, portion 46 nearer to the vane 16.

The large diameter portion 44 has external threads 48 and internal threads 50. The external threads 48 rigidly engage one end 52 of the torque shaft 14, while the internal threads 50 securely receive a cable fitting 54 which defines a central cavity (not shown).

The small diameter portion 46 defines a cavity which securely receives a vane attachment end member 56 of the vane 16. A retaining collar, or ring, 58 ensures that an annular protective plate 94 is secured to the transmission member 40. The small diameter portion has attached to it four piezoelectric transducers or strain gages 60 which are arrayed at substantially 90° relative to each other. These transducers 60 together measure the corresponding torque exerted on the small diameter portion 46 of the torque cell 38 during operating conditions and generate a signal representative of such torque. It will be appreciated that maximum angular deflection, indicative of strain, of the transmission member 40 occurs at the small diameter portion 46 which is adjacent the vane 16. Accordingly, a measurement of the torque or angular deflection of the small diameter portion 46 yields a highly accurate measurement of soil shear strength in the vicinity of the vane 16.

The torque cell 38 also advantageously includes other elements which preserve the accuracy of the torque measurements and quickly relay them to a read-out or output device 62 as shown in FIG. 1. In particular, the larger diameter portion 44 of the transmission member 40 may define four tubular passageways 64 and a generally cylindrical chamber 66 occupied by non-conductive, shrink tubes 68 and a lower end portion 70 of a cable 72. The passageways 64 serve as passages for transducer or gage wires 74 which transmit electrical signals from the transducers or gages 60. The chamber 66 securely receives the fitting 54 and the lower end portion 70 of the cable 72 which passes through the central cavity of the fitting 54.

The cable 72 includes wires 76, which are connected to the wires 74 and surrounded by the shrink tubes 68 in the area where they are connected. The wires 76 transfer the electrical signals transmitted by the wires 74 to the device 62. The shrink tubes 68 insulate the wires 72 and 76. Both the cable 72 and the wires 76 pass through the torque shaft 14 and are preferably connected to an amplifier 78, which boosts the electrical signal transferred to the device 62. The cable 72 is preferably held in place in the chamber 66 with the aid of the fitting 54 and a rubberized grommet 80.

The chamber 66 is also filled with an encapsulation material 82. This enhances the integrity of the electrical signals relayed by ensuring that the shrink tubes 68, and the wires 74 and 76 and cable 72 are held firmly in place and protected against moisture.

Figure 2:
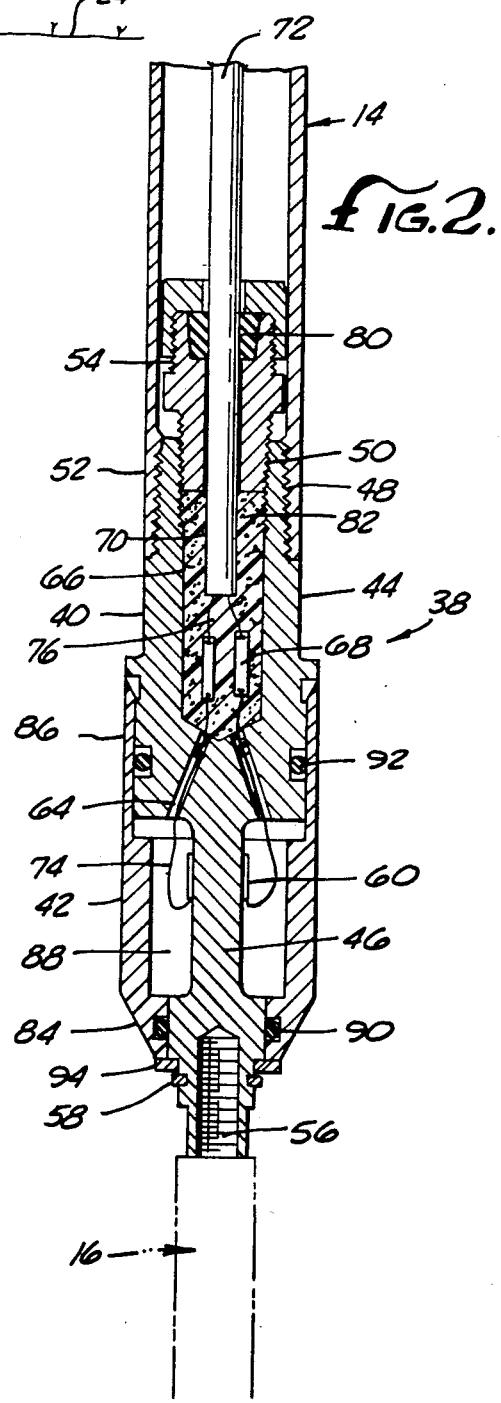
FIG. 2 is a cross-sectional view of the torque cell taken vertically along the central axis of the apparatus.

The housing 42 of the torque cell 38, as shown in FIG. 2, extends upwardly from the vane 16, is generally cylindrical and has a bottom end 84 and a top end 86. The bottom end 84 has a smaller opening which receives the small diameter portion 46 of the transmission member 40. The top end 86 has a larger opening which receives the large diameter portion 44 of the transmission member 40. This configuration gives the front portion of the torque cell 38 a pointed or tapered shape, thereby making it easier for the torque cell 38 to penetrate to a desired depth.

The housing 42 also defines an annular cavity 88 which surrounds the small diameter portion 46 of the transmission member 40. This feature protects the transducers or gages 60 and the transducer or gage wires 74 against moisture, abrasion and thermal gradients from the surrounding soil, all of which can impair the accuracy of the torque measurements.

The housing 42 is further connected to the transmission member 40 such that it can be easily removed, but produces negligible frictional forces which might otherwise impair the accuracy of the torque measurements. Additionally, a lower seal 90 disposed between the housing 42 and the small diameter portion 46 and an upper, or rear, seal 92 disposed between the housing 42 and the large diameter portion 44 facilitate the quick removal of the housing 42. As a result, the transducers or gages 60 and the transducer or gage wires 74 can be easily replaced without having to replace the vane 16. Conversely, if the vane 16 fails, there is no need to change the transducers or gages 60. Further, an annular protective plate 94 ensures that there is intimate contact between the lower seal 90 and the small diameter portion 46 and effectively protects the housing 42 from damage during installation and operation.

The housing 42 could, if not properly constructed, introduce inaccuracies into the torque measurements through a transmission of torque to the lower seal 90, by-passing the transmission member 40. However, due to its advantageous construction, the housing 42 is rotatable relative to the transmission member 40 at the top end thereof upon the angular deflection of the transmission member 40 in response to torque from the torque motor 12. In this embodiment, the housing rotates only about 0.003 to 0.005 inches. As a result, the lower seal 90 tends to minutely flex, rather than rub against the transmission member 40. This produces negligible inaccuracy such that the torque measurements conveyed by the transducers or gages 60 very closely approximate the torque exerted by the vane 16 on its surrounding soil. A pin (not shown) may also be placed in a slot extending through the transmission member 40 and located above the upper seal 92. This will then prevent the top end of the housing 42 from rotating relative to the transmission member 40. Since the housing 42 is pinned to the transmission member 40 above the strain gages 60, the torque required to overcome friction when the housing is rotated relative to the surrounding soil does not effect the strain gages.

The operation of a testing apparatus 10 embodying the torque cell 38 according to the present invention will now be described with reference to FIGS. 1 and 2. Initially, the vane 16 is connected to the torque cell 38 and positioned at a desired depth. The torque motor 12 then rotates the torque shaft 14, thereby transmitting torque through the torque cell 38 to the vane 16 which exerts torque on the surrounding soil. This torque is then measured by the transducers or gages 60 which together relay a measurement of the torque or angular deflection acting on the necked down, or small diameter, portion 46 to the read-out device 62 in the manner described above. Typically, the torque is applied to the soil until the soil has given way to the torque from the vane 16. Accordingly, the transducers or gages 60 transmit a series of torque measurements corresponding to the degrees of rotation of the vane 16. The shear strength of the surrounding soil can then be calculated by the following mathematical formula:

$$s = T \div K$$

where:
 s = shear strength of the soil
 T = torque or turning moment required to shear the soil
 K = a constant, depending on the dimensions and shape of the vane.

It will be appreciated from the foregoing description that the present invention provides an easily removable and replaceable torque cell, which quickly, economically and accurately provides a measurement of soil shear strength. Its advantageous location, directly above the vane, makes it impervious to inaccuracies produced by such phenomena as friction in the torque shaft support bearings and soil rubbing against the torque shaft as it rotates. Moreover, the torque cell makes it unnecessary to apply either corrective frictional equations or extrapolation techniques. Nor is there any need to manipulate and analyze numerous measurements from various sources to assess soil shear strength. The particular embodiment depicted in FIGS. 1-2 is included only by way of example. Those of ordinary skill in the art will appreciate that other configurations for a torque cell capable of measuring soil shear strength can be devised.

Although the invention has been described in detail with reference to the presently preferred embodiments, it will be appreciated by those of ordinary skill in the art that various modifications can be made without departing from the spirit and scope of the invention. Accordingly, the invention is limited only by the following claims.

I claim:

1. A testing apparatus for accurately measuring in situ the shear strength of soil through a measurement of the torque exerted on said soil by a vane to be inserted into said soil to a predetermined depth beneath the soil surface, comprising:
 motor means to be positioned at or near said soil surface for providing soil testing torque to said vane;
 a torque shaft extending downwardly from said motor means beneath said soil surface;
 a cable extending from said motor means and through said shaft; and
 a torque cell positioned immediately above said vane and adapted to provide a measurement of the torque exerted on said soil by said vane, including
 a fitting rigidly secured to said shaft and defining a central cavity which receives said cable,
 a torque transmission member by which torque is transmitted from said shaft to said vane, said transmission member including a large diameter portion nearer said shaft and a small diameter portion nearer to said vane where maximum angular deflection occurs, said large diameter portion defining a generally cylindrical chamber which securely receives said fitting and said cable.

an electrical transducer mounted on said transmission member for measuring the torque applied to said torque transmission member and generating a signal representative thereof, a generally cylindrical housing surrounding said transmission member and defining an annular cavity surrounding said small diameter portion, said transducer being disposed within said cavity and attached to said small diameter portion of said torque transmission member, said housing being free to rotate relative to said transmission member at one end thereof upon angular deflection of said transmission member in response to torque provided by said motor means, said housing having a bottom end with a smaller opening therein in which said small diameter portion is received and a top end with a larger opening therein in which said large diameter portion is received, a lower seal disposed between said small diameter portion and said housing, an upper seal disposed between said large diameter portion and said housing, a first wire leading from said transducer, wherein said cable includes a second wire connected to said first wire whereby said electronic signal from said transducer can be transmitted to said soil surface whereby said apparatus measures in situ the shear strength of said soil, and a conductive tube located within said chamber and surrounding said first wire and said second wire in the area where they are connected.

* * * * *